(12) United States Patent
Keefer et al.

(10) Patent No.: US 11,944,549 B2
(45) Date of Patent: Apr. 2, 2024

(54) 3D PRINTED MONOBLOCK ORTHOPAEDIC SURGICAL IMPLANT WITH CUSTOMIZED PATIENT-SPECIFIC AUGMENT

(71) Applicant: DEPUY SYNTHES PRODUCTS, INC., Raynham, MA (US)

(72) Inventors: Ryan C. Keefer, Warsaw, IN (US); Bernice A. Gatrell, Warsaw, IN (US); Andrew M. Hudson, Warsaw, IN (US); Christel M. Wagner, Warsaw, IN (US); Catherine Santis, Warsaw, IN (US); Daniel N. Huff, Warsaw, IN (US); Paul B. Sade, Sr., Warsaw, IN (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 162 days.

(21) Appl. No.: 17/219,554

(22) Filed: Mar. 31, 2021

(65) Prior Publication Data
US 2022/0313443 A1 Oct. 6, 2022

(51) Int. Cl.
*A61F 2/34* (2006.01)
*A61F 2/30* (2006.01)

(52) U.S. Cl.
CPC ............ *A61F 2/34* (2013.01); *A61F 2/30942* (2013.01); *A61F 2002/30957* (2013.01); *A61F 2002/30985* (2013.01); *A61F 2002/3432* (2013.01); *A61F 2002/345* (2013.01); *A61F 2002/348* (2013.01); *A61F 2310/00011* (2013.01); *A61F 2310/00179* (2013.01)

(58) Field of Classification Search
CPC ........................................................ A61F 2/34
See application file for complete search history.

(56) References Cited

U.S. PATENT DOCUMENTS 6,682,567 B1 * 1/2004 Schroeder ............. A61F 2/4609
623/22.24
10,456,262 B2 * 10/2019 Mistry ...................... A61F 2/34
(Continued)

FOREIGN PATENT DOCUMENTS

AU 2018204123 A1 1/2019
EP 3412252 A1 12/2018
(Continued)

OTHER PUBLICATIONS

PCT International Search Report for International Application No. PCT/IB2022/052985, dated Aug. 22, 2022, 9 pages.
(Continued)

*Primary Examiner* — Brian A Dukert
(74) *Attorney, Agent, or Firm* — Barnes & Thornburg LLP

(57) ABSTRACT

An acetabular shell component includes a solid substrate, a porous outer layer coupled to the solid substrate, a porous inner layer coupled to the solid substrate, and an inner bearing coupled to the porous inner layer. One or more adjuncts extend outward from the porous outer layer. Each adjunct includes an outer surface that defines a customized patient-specific negative contour shaped to conform to a positive contour of a patient's bone. A method for manufacturing the acetabular shell component using an additive manufacturing process is also disclosed.

6 Claims, 7 Drawing Sheets

(56) References Cited

U.S. PATENT DOCUMENTS

| | | | |
|---|---|---|---|
| 2013/0035766 A1* | 2/2013 | Meridew | A61F 2/34 |
| | | | 623/22.21 |
| 2013/0199259 A1 | 8/2013 | Smith | |
| 2013/0231750 A1* | 9/2013 | Taylor | A61F 2/34 |
| | | | 623/22.21 |
| 2015/0359638 A1 | 12/2015 | Khowaylo et al. | |
| 2017/0143495 A1 | 5/2017 | Dunn et al. | |
| 2017/0296699 A1 | 10/2017 | Khowaylo et al. | |
| 2018/0036129 A1* | 2/2018 | Mistry | A61F 2/30734 |
| 2018/0353642 A1 | 12/2018 | Lee et al. | |

FOREIGN PATENT DOCUMENTS

| | | | |
|---|---|---|---|
| WO | 2015191956 A1 | 12/2015 | |
| WO | 2017/098039 A1 | 6/2017 | |

OTHER PUBLICATIONS

PCT Partial International Search Report for International Application No. PCT/IB2022/052985, dated Jun. 22, 2022, 13 pages.

\* cited by examiner

3D PRINTED MONOBLOCK ORTHOPAEDIC SURGICAL IMPLANT WITH CUSTOMIZED PATIENT-SPECIFIC AUGMENT

TECHNICAL FIELD

The present disclosure relates generally to orthopaedic surgical implants and, more particularly, to customized patient-specific orthopaedic surgical implants.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A prosthetic hip joint generally includes an acetabular prosthetic component and a femoral head prosthetic component. The acetabular prosthetic component may be embodied as a modular acetabular prosthetic component or a monoblock acetabular. Typical modular acetabular prosthetic components include a modular outer shell configured to engage the acetabulum of the patient and a removable inner bearing or liner that may be coupled to the shell and configured to engage the femoral head. The femoral head prosthetic component and inner liner of the acetabular component form a ball and socket joint that approximates the natural hip joint.

Conversely, typical monoblock acetabular prosthetic components include an integral shell and bearing component. However, standard manufacturing techniques for such typical monoblock components do not allow for holes or other fixation guides to pass through the shell component.

Another type of prosthetic hip joint is a constrained hip joint, which includes mechanical features such as retaining rings in order to reduce the likelihood of dislocation. However, typical constrained hips have a reduced range of motion compared to other prosthetic hip designs.

SUMMARY

According to one aspect, a monoblock acetabular shell component includes a solid substrate, a porous outer layer coupled to the solid substrate, a porous inner layer coupled to the solid substrate, an inner bearing coupled to the porous inner layer, and an adjunct extending outwardly from the porous outer layer. The porous outer layer and the porous inner layer each have a porosity greater than the solid substrate. The inner bearing includes a bearing surface, and the bearing surface defines a cavity sized to receive an orthopaedic implant component. The adjunct includes an outer surface that defines a customized patient-specific negative contour shaped to conform to a positive contour of a patient's bone. In an embodiment, the solid substrate, the porous outer later, the porous inner layer, and the adjunct comprise an additively manufactured component.

In an embodiment, the solid substrate, the porous outer later, the porous inner layer, and the inner bearing have a combined thickness of about 3 millimeters.

In an embodiment, each of the solid substrate, the porous outer layer, and the porous inner layer comprises a metallic material. In an embodiment, each of the solid substrate, the porous outer layer, and the porous inner layer comprises a ceramic material. In an embodiment, the inner bearing comprises a polymeric material. In an embodiment, each of the solid substrate, the porous outer layer, the porous inner layer, and the inner bearing comprises a ceramic material.

In an embodiment, an aperture is defined through the outer surface of the adjunct. The aperture is sized to receive a fastener.

In an embodiment, the bearing surface defines a cavity sized to receive a polymeric dual mobility bearing. In an embodiment, the bearing surface defines a cavity sized to receive a constrained femoral head component.

According to another aspect, a method for manufacturing an orthopaedic prosthetic includes identifying a positive contour of a patient's bone based on one or more medical images of the patient's bone; and additively manufacturing a monoblock acetabular shell component, wherein the monoblock acetabular shell component comprises an adjunct extending outwardly from the monoblock acetabular shell component, wherein the adjunct comprises an outer surface that defines a customized patient-specific negative contour shaped to conform to the positive contour of a patient's bone.

In an embodiment, identifying the positive contour includes generating a three-dimensional model of the patient's bone based on the one or more medical images of the patient's bone.

In an embodiment, the method further includes capturing the one or more medical images of the patient's bone. Identifying the positive contour includes identifying the positive contour in response to capturing the one or more medical images.

In an embodiment, additively manufacturing the monoblock acetabular shell component includes additively manufacturing a solid substrate, a porous outer layer coupled to the solid substrate, and a porous inner layer coupled to the solid substrate, wherein the adjunct is coupled to the porous outer layer, and wherein each of the porous outer layer and the porous inner layer has a porosity greater than the solid substrate. In an embodiment, additively manufacturing the monoblock acetabular shell component further includes additively manufacturing an inner bearing coupled to the porous inner layer, wherein the inner bearing comprises a bearing surface. In an embodiment, the inner bearing comprises a ceramic material.

In an embodiment, the method further includes manufacturing an inner bearing coupled to the porous inner layer of the monoblock acetabular shell component, wherein the inner bearing comprises a bearing surface. In an embodiment, manufacturing the inner bearing includes injection molding the inner bearing or compression molding the inner bearing. In an embodiment, the inner bearing comprises a polymeric material. In an embodiment, the shell component comprises a metallic material. In an embodiment, the shell component comprises a ceramic material.

In an embodiment, additively manufacturing the monoblock acetabular shell component includes forming an aperture defined through the outer surface of the adjunct, wherein the aperture is sized to receive a fastener.

BRIEF DESCRIPTION OF THE DRAWINGS

The detailed description particularly refers to the following figures, in which.

DETAILED DESCRIPTION OF THE DRAWINGS

Figure 1:
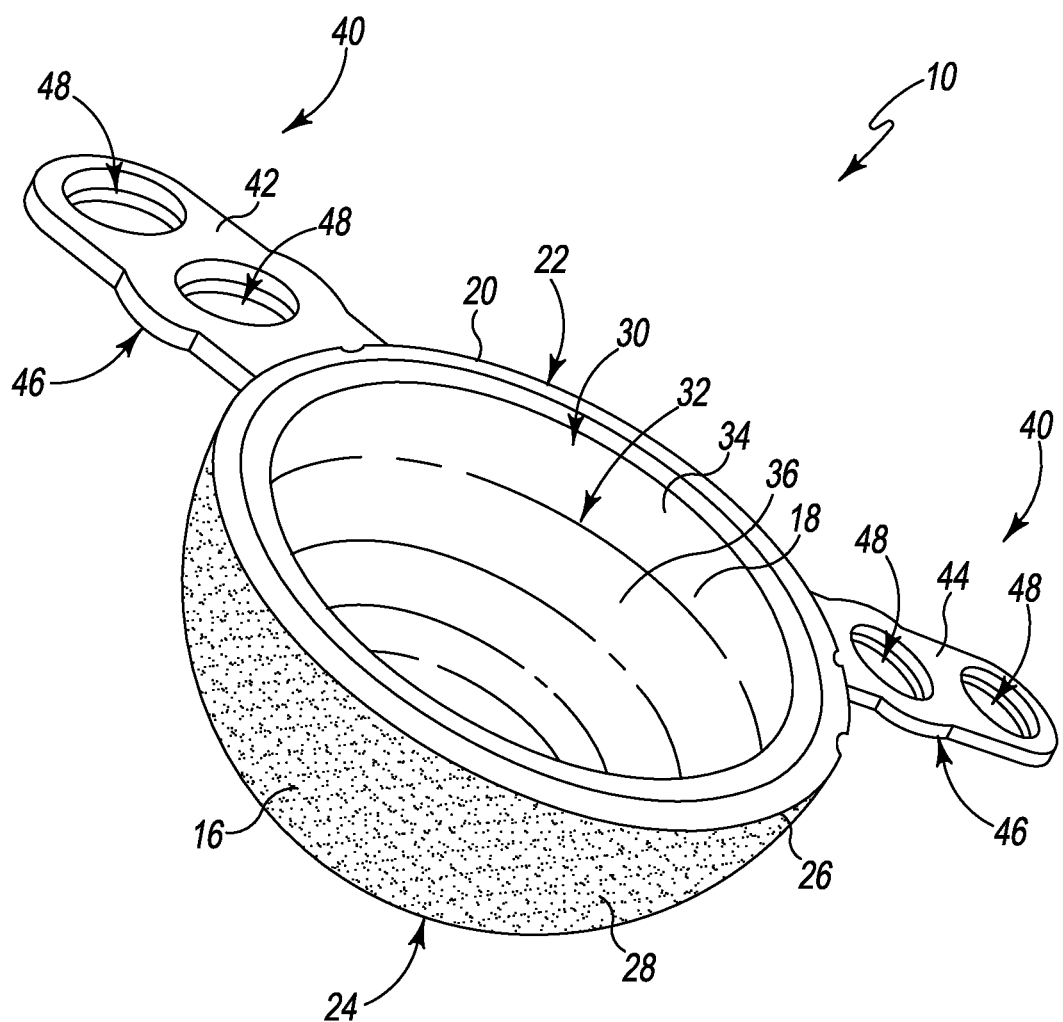
FIG. 1 is a perspective view of an embodiment of a monoblock acetabular shell component.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
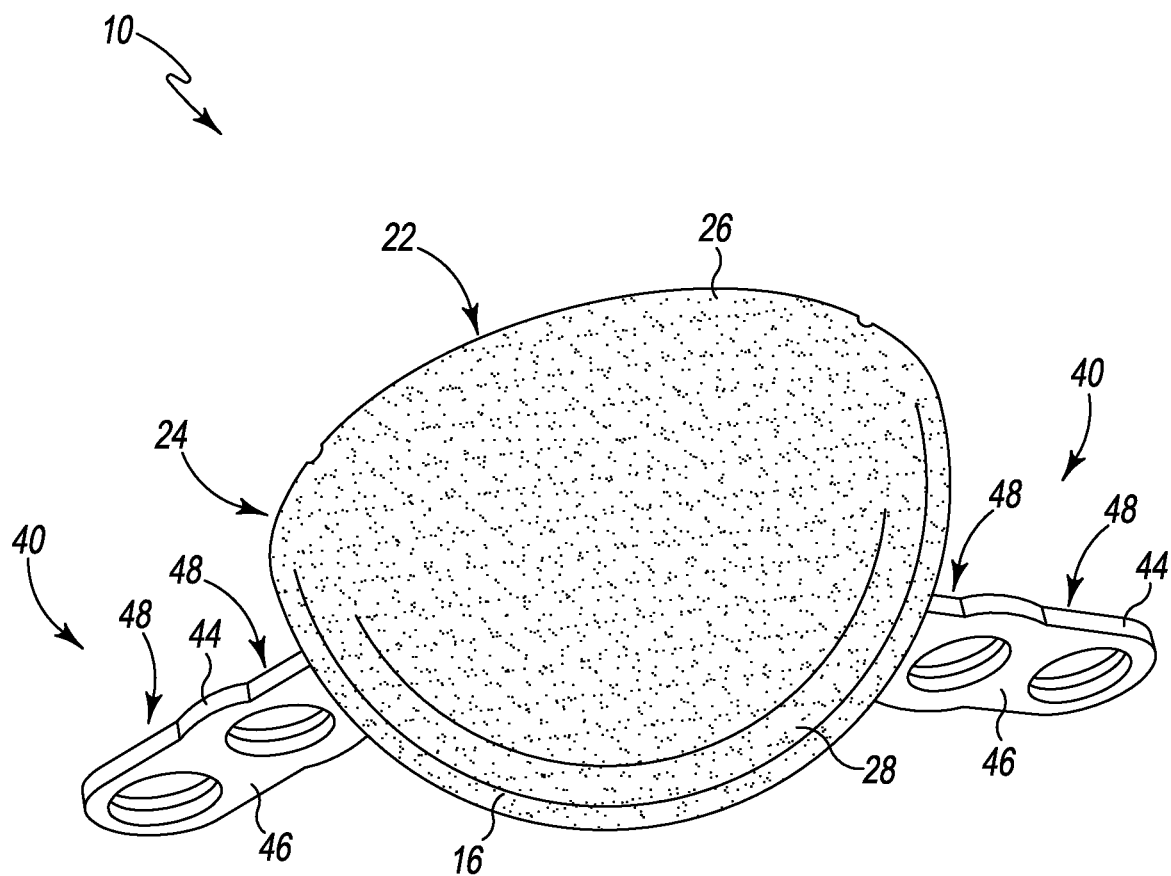
FIG. 2 is a rear perspective view of the monoblock acetabular shell component of FIG. 1.
Figure 3:
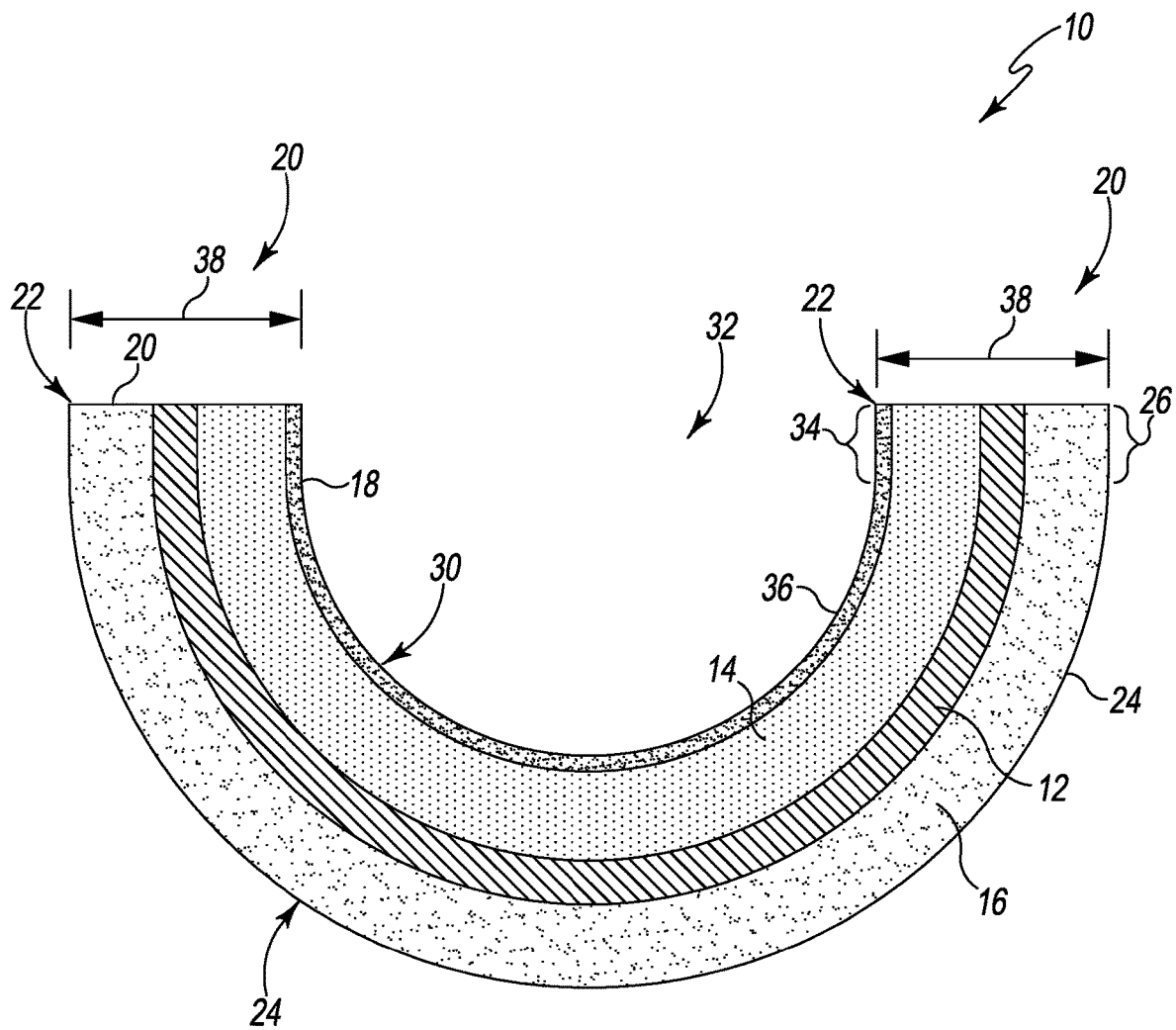
FIG. 3 is a cross-sectional view of the monoblock acetabular shell component of FIGS. 1-2.

Referring now to FIGS. 1-3, an illustrative 3D-printed, monoblock acetabular prosthetic shell component 10 is shaped to be implanted in a surgically-prepared acetabulum of a patient's pelvis. The shell component 10 is manufactured using an additive manufacturing process. The additive manufacturing process may include one or more forms of additive manufacturing technology such as, for example, Selective Laser Sintering (SLS), Direct Metal Laser Sintering (DMLS), Directed Energy Deposition (DED), 3D printing, or other additive manufacturing technology. In such an additive manufacturing processes, the shell component 10 may be manufactured as a unitary component formed from multiple layers of material that are deposited during the manufacturing process. In some embodiments, the shell component 10 may be formed from an implant-grade, biocompatible metallic material such as titanium, cobalt, chromium, molybdenum, tantalum, and mixtures thereof. Additionally or alternatively, in some embodiments the shell component 10 may be formed from a ceramic material such as alumina, zirconia, or zirconia toughened alumina (ZTA).

As shown in the cross-sectional view of FIG. 3, the shell component 10 includes a solid substrate 12, a porous inner layer 14, and a porous outer layer 16. The substrate 12 and the porous layers 14, 16 are formed as a unitary component using an additive manufacturing process, and thus may be formed from the same material (e.g., a metallic material such as titanium or a ceramic material). Each of the porous layers 14, 16 has a porosity greater than a porosity of the solid substrate 12. In some embodiments, each of the porous layers 14, 16 may have a different porosity. In some embodiments, the porosity of each of the porous layers 14, 16 may be the same.

In some embodiments, the porous outer layer 18 may have a 3D printed lattice structure intended for bone ingrowth for non-cemented applications. In those embodiments, 3D printed lattice structure may have interconnected volume porosity between 20% to about 80%, and may have pores of 50 to 500 microns. In some embodiments, the 3D printed lattice structure may have a maximum thickness of 800 microns. For example, in an embodiment, the 3D printed lattice structure may have a thickness of 762±254 microns. Additionally or alternatively, in some embodiments the 3D printed lattice structure may have a larger maximum thickness of about 1500 microns with the assistance of a bone growth enhancement element such as hydroxyapatite (HA).

The shell component 10 further includes an inner integrated bearing 18 formed into or otherwise embedded within the porous inner layer 14. The integrated bearing 18 may be compression molded, injection molded, or 3D printed into the porous inner layer 14. In some embodiments, the integrated bearing 18 may be formed from a polymeric material such as highly crosslinked polyethylene (PE), antioxidant filled PE, or other polymers such as polyether ether ketone (PEEK). In other embodiments, the integrated bearing 18 may be formed from a ceramic material (i.e., 3D printed ceramic). In certain of those embodiments, the integrated bearing 18, the solid substrate 12, and the porous layers 14, 16 may all be formed from a ceramic material. Additionally or alternatively, in some embodiments the integrated bearing 18 may be formed from ceramic and the solid substrate 12 and the porous layers 14, 16 may be formed from a metallic material such as titanium.

Referring again to FIGS. 1-3, the shell component 10 has a distal rim 20 that includes a flat rim surface 22. An outer wall 24 extends from the distal rim 20. The illustrative outer wall 24 includes an annular outer surface 26 that extends from the distal rim 20 to a convex curved outer surface 28. The curved outer surface 28 may have a standard size and/or shape that is common to other implants (and/or is selected from a group of standard implant sizes and/or shapes). For example, in the illustrative embodiment, the convex curved outer surface 28 is semi-spherical and shaped to match the shape of a patient's surgical prepared acetabulum. The annular outer surface 26 is illustratively a cylindrical extension of the curved outer surface 28, which may increase jump distance of the shell component 10, thereby reducing likelihood of dislocation. As shown, the outer wall 24 is formed by the porous outer layer 16, which permits bone to affix biologically to the shell component 10 after implantation, thus improving fixation.

Figure 4:
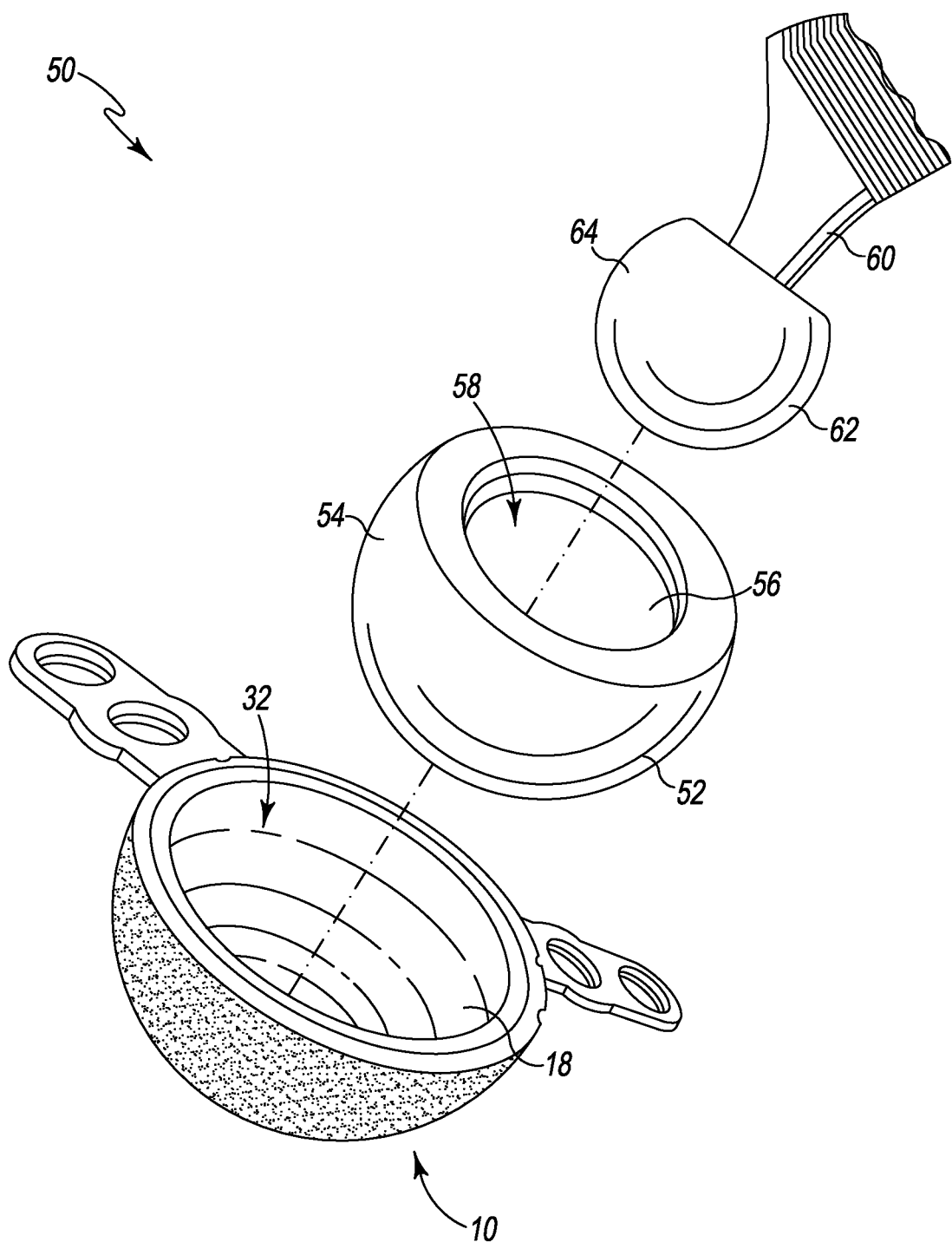
FIG. 4 is a perspective view of a dual mobility prosthetic implant system including the monoblock acetabular shell component of FIGS. 1-3.
Figure 5:
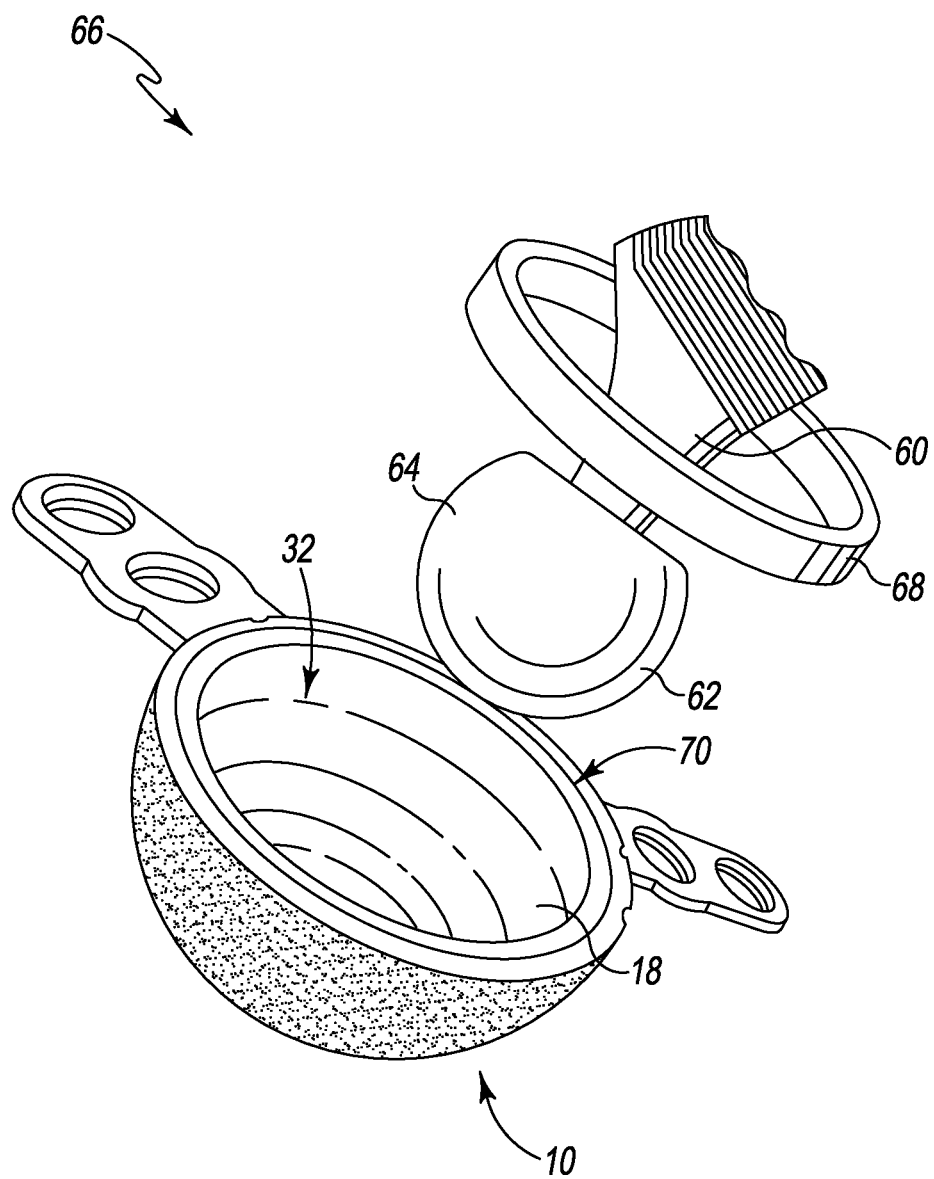
FIG. 5 is a perspective view of a constrained liner prosthetic implant system including the monoblock acetabular shell component of FIGS. 1-3.

The shell component 10 further includes an inner wall 30 formed by the integrated bearing 18 that extends inwardly from the distal rim 20 to define a cavity 32 in the shell component 10. The inner wall 30 of the shell component 10 includes an annular inner surface 34 that is positioned opposite the annular outer surface 26, and a concave curved inner surface 36 that is positioned opposite the convex curved outer surface 28. The cavity 32 is sized to receive a prosthetic component such as a femoral head component (not shown), which may be formed from a metallic material, a ceramic material, or other material. In other embodiments, the cavity 32 may be sized to receive a mobile bearing, a captive femoral head, or other prosthetic component. For example, and as described further below, FIG. 4 illustrates a shell component 10 configured to receive a dual mobility bearing, and FIG. 5 illustrates a shell component 10 configured to receive a captive femoral head.

A shown in FIG. 3, the outer wall 34 of the outer porous layer 16 and the inner wall 30 of the integrated bearing 18 define a thickness 38 of the shell component 10. In some embodiments, the thickness 38 may be constant throughout the shell component 10 or the thickness 38 may vary between parts of the shell component 10. In many embodiments, the thickness 38 is thinner than a corresponding combined thickness of a typical modular acetabular shell and liner assembly. Additionally, due to the additive manufacturing process used for manufacturing the shell component 10, in some embodiments the thickness 38 may also be thinner than a corresponding thickness of a conventionally manufactured monoblock shell component. Thus, by having a relatively smaller thickness 38, the shell component 10 may be adapted to receive a relatively larger femoral head component as compared to typical modular acetabular shell components, which may reduce the likelihood of dislocation and/or improve the range of motion for the shell component 10. For example, in some embodiments, the combined thickness 38 of the shell component 10 may be in a range from about 1.5 millimeters to about 5 millimeters. As a further example, in some embodiments, the combined thickness 38 of the shell component 10 may be about 3 millimeters.

Referring again to FIGS. 1-2, the shell component 10 further includes one or more patient-specific adjuncts 40. Each of the adjuncts 40 may be embodied as a wing, a buttress, a void filler, a flange, or other structure that includes patient-specific geometry that matches at least a part of the patient's bone. For example, the illustrative shell component 10 includes a pair of flanges 42, 44 extending from the annular outer surface 26. Each adjunct 40 may be formed as a part of or otherwise attached to the solid substrate 12 of the shell component 10. Additionally or alternatively, in some embodiments, each adjunct 40 may include or otherwise be part of the porous outer layer 16. As shown, each adjunct 40 includes an outer profiled surface 46. Each surface 46 may include one or more negative contours that match and receive a corresponding positive contour of the patient's bony geometry. Additionally, one or more apertures 48 or other fixation guides may be defined through each adjunct 40. Each of the apertures 48 is sized or otherwise adapted to receive a fastener such as a bone screw or pin, which may be used to secure the shell component 10 to the patient's bone.

By inclusion of one or more adjuncts 40 each having a profiled outer surface 46, the shell component 10 is thus a customized patient-specific orthopaedic implant. What is meant herein by the term "customized patient-specific orthopaedic implant" is a surgical implant or prosthesis for use by a surgeon in performing an orthopaedic surgical procedure that is intended, and configured, for use on a particular patient. As such, it should be appreciated that, as used herein, the term "customized patient-specific orthopaedic surgical implant" is distinct from standard, non-patient-specific orthopaedic surgical implants that are not fabricated or customized to any particular patient.

In use, the negative contours included in the outer surface 46 of each adjunct 40 match and receive corresponding positive contours of the patient's bony geometry, causing the adjuncts 40 to engage the positive contours of the patient's bone in a predetermined position and/or orientation. Thus, the outer profiled surface 46 of each adjunct 40 achieves intimate contact with the patient's bone, which may improve fixation of the shell component 10. Additionally, as described above, because of the reduced thickness 38 achieved by use of a monoblock construction, the shell component 10 may allow for use of larger femoral head component as compared to a modular liner, which may improve resistance to dislocation. Further, because the patient-specific adjuncts 40 support screw fixation, the shell component 10 may improve fixation and in particular improve initial fixation prior to bone ingrowth as compared to typical monoblock implants, which typically do not include holes or other fixation guides for screw fixation.

Referring now to FIG. 4, in some embodiments the monoblock acetabular shell component 10 may be used with a dual mobility prosthetic hip system 50. The illustrative dual mobility hip system 50 includes the shell component 10, a mobile bearing 52, and a femoral component 60. The mobile bearing 52 is formed from a polymeric material such as such as highly crosslinked polyethylene (PE), ultra-high-molecular-weight (UHMW) PE, antioxidant filled PE, or other polymers such as polyether ether ketone (PEEK). As shown, the mobile bearing 52 includes a convex curved outer wall 54 and a concave curved inner wall 56. The curved inner wall 56 defined a cavity 58. The femoral component 60 includes a femoral head 62 having a convex curved outer wall 64. The femoral head 62 may be formed from a metallic material such as titanium or a ceramic material.

As shown in FIG. 4, the cavity 32 defined by the inner wall 30 of the shell component 10 is sized to receive the outer wall 54 of the mobile bearing 52. Similarly, the cavity 58 defined by the inner wall 56 of the mobile bearing 52 is sized to receive the outer wall 64 of the femoral head 62. In use, the outer wall 54 of the mobile bearing 52 may articulate against the integrated bearing 18 of the shell component 10. At extremes of range of motion for the dual mobility hip system 50, the outer wall 64 of the femoral head 62 may also articulate against the inner wall 56 of the mobile bearing 52. As compared to typical dual mobility hip prosthesis systems, the system 50 including the shell component 10 may accommodate a larger size of femoral head 62 and thus may improve dislocation resistance.

Referring now to FIG. 5, in some embodiments the monoblock acetabular shell component 10 may be used with a constrained liner prosthetic hip system 66. The illustrative constrained liner hip system 66 includes the shell component 10, the femoral component 60, and a retaining ring 68. As described above, the femoral component 60 may be formed from a metallic material or a ceramic material, and includes a femoral head 62 having a convex curved outer wall 64. The retaining ring 68 may be formed from a metallic material such as titanium. As shown, the cavity 32 defined by the inner wall 30 of the shell component 10 is sized to receive the outer wall 64 of the femoral head 62. The shell component 10 further includes a groove 70 defined in the rim surface 22 of the distal rim 20. The groove 70 is sized to receive the retaining ring 68. In use, the outer wall 64 of the femoral head 62 articulates against the integrated bearing 18. The retaining ring 68, positioned within the groove 70, mechanically captures the femoral head 62 within the cavity 32 of the shell component 10. As compared to typical mechanically constrained hip systems, the system 66 including the shell component 10 has a reduced thickness 38 and thus may accommodate a larger size of femoral head 62. Accordingly, the system 66 may support a larger range of motion as compared to typical constrained hips.

Figure 6:
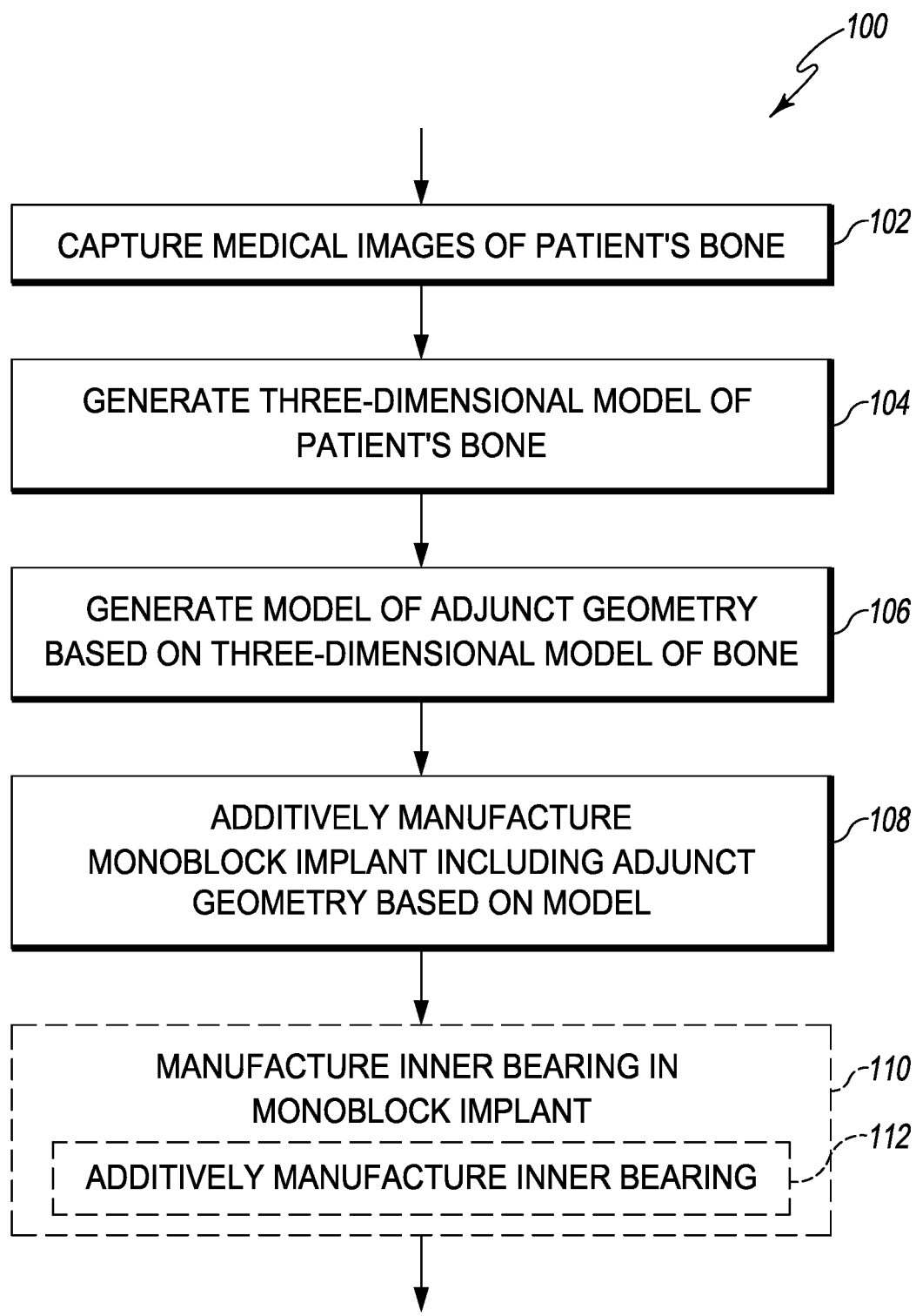
FIG. 6 is a simplified flow diagram of a method for manufacturing a monoblock acetabular shell component as shown in any of FIGS. 1-5.

Referring now to FIG. 6, a method 100 for manufacturing the acetabular shell component 10 is illustrated. The method 100 begins in process step 102, in which a number of medical images of the patient's bone are captured. To do so, an orthopaedic surgeon or other healthcare provider may operate an imaging system to generate the medical images. The medical images may be embodied as any number and type of medical images capable of being used to generate a three-dimensional rendered model of the patient's bony anatomy or relevant joint. For example, the medical images may be embodied as a number of X-ray images or other two-dimensional images from which a three-dimensional rendered model of the patient's relevant bony anatomy may be generated. Additionally, in some embodiments, the medical image may be enhanced with a contrast agent designed to highlight the cartilage surface of the patient's joint. Additionally or alternatively, the medical images may be embodied as any number of computed tomography (CT) images, magnetic resonance imaging (MRI) images, or other three-dimensional medical images.

In process step 104, a three-dimensional model of the patient's bone is generated. For example, in some embodiments, a computing device or other modeling system may perform an x-ray segmentation process to model the patient's bone based on the input medical images. The resultant three-dimensional model includes contours and other surface geometry of the patient's acetabulum, for example bony landmarks such as the transverse acetabular ligament (TAL) or other bony features. In other embodiments, any other appropriate technique may be performed to generate a three-dimensional model of the patient's bone based on the medical images.

In process step 106, a three-dimensional model of adjunct 40 geometry is generated based on the three-dimensional model of the patient's bone. The three-dimensional model of each adjunct 40 includes geometry describing the outer surface 46 of the adjunct 40. Thus, the three-dimensional model for each adjunct 40 includes one or more negative contours that match and receive a corresponding positive contour of the patient's bony geometry that is captured in the corresponding model. Thus, when positioned in the patient's acetabulum, the outer surface 46 of each adjunct 40 engages one or more corresponding positive contours of the patient's bone, allowing for adjunct fixation of the shell component 10. Further, the outer surface 46 of each adjunct 40 may engage the positive contours of the patient's bone in a predetermined position and/or orientation, which may further improve fixation of the shell component 10.

In some embodiments, during the manufacturing process, the surgeon or other operator may position the one or more adjuncts 40 on the shell component 10, for example using a preoperative planning user interface or other design tool. Additionally or alternatively, the one or more adjuncts 40 may be generated and/or positioned automatically relative to the shell component 10. For example, in some embodiments a computing device or other modeling system may morph or otherwise adapt predetermined geometry of a library adjunct to match the three-dimensional model of the patient's bone. After generating the three-dimensional model of the adjunct 40 geometry, that model may be added to or otherwise combined with other geometry of the acetabular shell component 10 for manufacturing purposes. For example, a final model may be generated as the union of multiple models including the patient-specific adjuncts 40.

In process step 108, the acetabular shell component 10 including one or more adjuncts 40 is additively manufactured. As described above, the shell component 10 may be manufactured using one or more forms of additive manufacturing technology such as, for example, Selective Laser Sintering (SLS), Direct Metal Laser Sintering (DMLS), Directed Energy Deposition (DED), 3D printing, or other additive manufacturing technology. The shell component 10 may thus be formed from metallic material, ceramic material, or another additively manufactured material. The additive manufacturing process may produce the outer porous layer 16, the solid substrate 12, and the inner porous layer 14 as a unitary component.

In some embodiments, in process step 110 the integrated inner bearing 18 may be manufactured in the shell component 10. As described above, in some embodiments, the integrated bearing 18 may be compression molded, injection molded, or otherwise molded into the inner layer 14. In those embodiments, the integrated bearing 18 may be formed from a polymeric material such as such as highly crosslinked polyethylene (PE), antioxidant filled PE, or other polymers such as polyether ether ketone (PEEK).

In some embodiments, in process step 112 the inner bearing 18 may be additively manufactured. In those embodiments, the inner bearing 18 may be formed from a polymeric material or a ceramic material (e.g., using ceramic 3D printing). In some embodiments, the shell component 10 and the integrated bearing 18 may be manufactured using the same additive manufacturing process. For example, in some embodiments a unitary shell component 10 including the integrated bearing 18 may be additively manufactured using a ceramic material. After additively manufacturing the shell component 10, the method 100 is completed.

Figure 7:
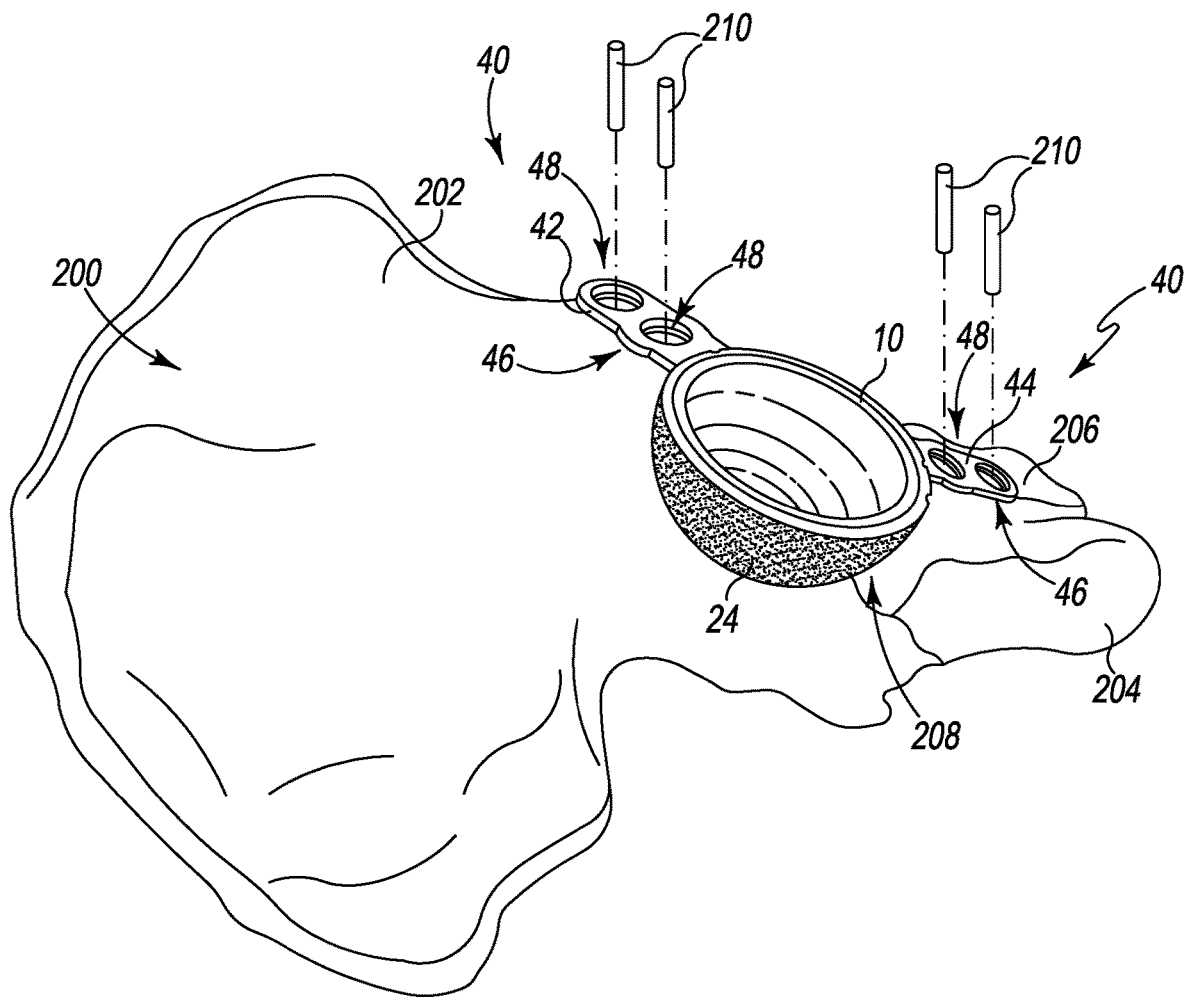
FIG. 7 is a perspective view showing the monoblock acetabular shell component of FIGS. 1-5 installed in a patient's hip.

Referring now to FIG. 7, in use, the additively manufactured acetabular shell component 10 may be used during an orthopaedic surgical procedure. FIG. 7 illustrates a patient's hip bone 200. As shown, the hip bone 200 includes three parts, an ilium 202, an ischium 204, and a pubis 206, that define a natural acetabulum 208. To perform the orthopaedic surgical procedure, first, the surgeon surgically prepares the patient's bone to receive the prosthetic assembly 10. For example, the surgeon may utilize a surgical reamer to prepare the patient's acetabulum 208 to receive the prosthetic assembly 10. In some embodiments, the surgeon may also remove any existing acetabular component or other prosthetic components from the patient's bone.

The surgeon next inserts the shell component 10 into the patient's surgically prepared acetabulum 208 until the outer surface 46 of the adjuncts 40 and/or the outer wall 24 contact the patient's bone 200. For example, in the illustrative embodiment, the surface 46 of the flange 42 contacts the ilium 202 and the surface 46 of the flange 44 contacts the ischium 204. The surgeon may assess whether intimate contact is achieved between the adjuncts 40 and the bone 200 or otherwise assess stability of the shell component 10 in the bone 200.

After positioning the shell component 10 in the surgically prepared acetabulum 208, the shell component 10 may be impacted or otherwise fixed into a final position and orientation. In some embodiments, one or more bone screws 210 or other fasteners may be used to attach the adjuncts 40 to the bone 200. For example, in the illustrative embodiment, the bone screws 210 may be inserted through the apertures 48 in order to secure the respective flanges 42, 44 to the bone 200. Accordingly, after implantation, the shell component 10 may be securely attached or otherwise fixed to solid bone of the patient.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. A monoblock acetabular shell component, the shell component comprising:
   a solid substrate;
   a porous outer layer coupled to the solid substrate, wherein the porous outer layer has a porosity greater than the solid substrate;
   a porous inner layer coupled to the solid substrate, wherein the porous inner layer has a porosity greater than the solid substrate; and
   an inner bearing coupled to the porous inner layer, wherein the inner bearing comprises a bearing surface and wherein the bearing surface defines a cavity sized to receive an orthopaedic implant component;
   wherein the solid substrate or the porous outer layer includes a patient-specific adjunct integrally formed therewith and extending outwardly from the porous outer layer, wherein the patient-specific adjunct comprises an outer surface, and wherein the outer surface defines a customized patient-specific negative contour shaped to conform to a positive contour of a patient's bone; and
   wherein each of the solid substrate, the porous outer layer, the porous inner layer, and the inner bearing comprises a ceramic material.

2. The shell component of claim 1, wherein the solid substrate, the porous outer later, the porous inner layer, and the patient-specific adjunct comprise an additively manufactured component.

3. The shell component of claim 1, wherein the solid substrate, the porous outer later, the porous inner layer, and the inner bearing have a combined thickness of about 3 millimeters.

4. The shell component of claim 1, wherein an aperture is defined through the outer surface of the patient-specific adjunct, wherein the aperture is sized to receive a fastener.

5. The shell component of claim 1, wherein the bearing surface defines a cavity sized to receive a polymeric dual mobility bearing.

6. The shell component of claim 1, wherein the bearing surface defines a cavity sized to receive a constrained femoral head component.

* * * * *